United States Patent [19]

Fitts et al.

[11] Patent Number: 5,142,648
[45] Date of Patent: Aug. 25, 1992

[54] METHOD AND APPARATUS FOR PAINT INSPECTION

[75] Inventors: John M. Fitts, Santa Monica, Calif.; Douglas M. Linn, Walled Lake, Mich.; Nilesh C. Thakker, West Hills, Calif.

[73] Assignee: General Motors Corporation, Detroit, Mich.

[21] Appl. No.: 562,059

[22] Filed: Aug. 2, 1990

[51] Int. Cl.⁵ .......................................... G01N 21/55
[52] U.S. Cl. ........................ 364/551.01; 364/526; 356/446
[58] Field of Search ............... 364/526, 525, 551.01, 364/576, 468, 553; 356/446, 237; 250/275; 382/8, 43

[56] References Cited

U.S. PATENT DOCUMENTS

| | | | |
|---|---|---|---|
| 3,193,690 | 7/1965 | Murata et al. | 250/232 |
| 3,771,879 | 11/1973 | Chambu et al. | 356/201 |
| 3,938,892 | 2/1976 | Klingman, III | 356/124 |
| 4,145,140 | 3/1979 | Fujii | 356/360 |
| 4,394,683 | 7/1983 | Liptay-Wagner | 358/107 |
| 4,448,527 | 5/1984 | Milana | 356/237 |
| 4,506,980 | 3/1985 | Pryor et al. | 356/237 |
| 4,527,898 | 7/1985 | Stapleton | 356/446 |
| 4,558,948 | 12/1985 | Picard | 356/124 |
| 4,586,817 | 5/1986 | Ehemann, Jr. | 356/124.5 |
| 4,629,319 | 12/1986 | Clarke et al. | 356/237 |
| 4,635,213 | 1/1987 | Murata et al. | 364/526 |
| 4,647,197 | 3/1987 | Kitaya et al. | 356/239 |
| 4,653,909 | 3/1987 | Kuperman | 356/124.5 |
| 4,679,075 | 7/1987 | Williams et al. | 358/106 |
| 4,715,709 | 12/1987 | Sekine et al. | 356/237 |
| 4,717,259 | 1/1988 | Suga | 356/446 |
| 4,746,805 | 5/1988 | Stapleton | 356/446 |
| 4,759,072 | 7/1988 | Yamane et al. | 382/8 |
| 4,803,374 | 2/1989 | Monfort et al. | 250/571 |
| 4,807,991 | 2/1989 | Carew | 356/72 |

Primary Examiner—Parshotam S. Lall
Assistant Examiner—Ellis B. Ramirez
Attorney, Agent, or Firm—Charles E. Leahy

[57] ABSTRACT

Video monitors sequentially displaying coarse bar patterns of various spatial frequencies are spaced two feet or more from a painted surface to be inspected. Video cameras, also spaced far from the surface, view the images reflected from the paint and a computer system analyzes the images by determining the modulation transfer function (MTF) of each reflecting surface. Surface curvature is compensated for by selecting the spatial frequencies in the sequence of patterns in accordance with the effect of the curvature on a reference pattern. The area under the MTF curve correlates to the distinctness of image of the surface and the area under the low spatial frequency portion of the curve correlates to orange peel.

12 Claims, 6 Drawing Sheets

METHOD AND APPARATUS FOR PAINT INSPECTION

FIELD OF THE INVENTION

This invention relates to the measurement of the finish quality of painted surfaces and particularly to the method and apparatus for measuring orange peel and distinctness of image.

BACKGROUND OF THE INVENTION

Painted articles have varying degrees of surface roughness or irregularity which may be unacceptable to users of the articles. Automotive vehicles and appliances, for example, have high quality requirements for paint appearance. A common type of paint condition is orange peel which comprises roughly sinusoidal surface undulations or bumps greater than 0.5 mm diameter. To determine acceptable quality of a painted product it is necessary to measure the severity of orange peel and compare it to known standards. The common practice for measuring orange peel is to subjectively compare standard panels with the article being inspected. Such subjective inspection is marked by inconsistency due in part to different inspectors. There have been some instruments proposed to measure orange peel.

Another measure of paint surface quality is distinctness of image or DOI. This measures a composite of orange peel, texture and gloss. Texture and gloss refer to surface roughness smaller than orange peel and extending into the microscopic range. To determine DOI the clarity of reflection of a standard pattern is graded by subjectively observing the reflection and assigning a figure of merit to the surface in accordance with the observer's judgment of the distinctness of the image. An instrument for measuring the DOI of a surface is disclosed in the U.S. Pat. No. 4,527,898 to Stapleton. That patent discloses a meter in contact with the surface for projecting a light onto the surface and sensing the reflected beam by a detector, chopping the beam by a motor driven blade, and a circuit for determining the rate of change of the detector signal, the rate of change being a measure of DOI. A table is used to correlate the measured rate of change to the subjective DOI scale.

It is desirable to use instruments to obtain objective paint quality measurements. Such instruments have limited usefulness when they require contact with the surface. When applied to automotive vehicles it is advantageous to make the surface measurements from a remote location so that the instrument does not interfere with other activities and allows vehicle motion during the measurement. In addition it is preferred that continuous or repetitive measurements ensue as the vehicle passes through an inspection station.

SUMMARY OF THE INVENTION

It is therefore an object of the invention to provide a method of remotely inspecting a painted surface to objectively measure orange peel and/or distinctness of image. It is a further object to provide such a method operable during movement of the surface. Still another object of the invention is to provide an apparatus for practicing the method.

The invention is carried out by the method of measuring the orange peel and/or distinctness of image of a painted surface comprising the steps of: generating a plurality of bar patterns each having a spatial frequency different from the other patterns, serially reflecting images of the patterns from the surface to be inspected, electronically imaging the reflected patterns, analyzing the images and generating modulation transfer function curves, and determining the surface quality from the modulation transfer function.

The invention is further carried out by a system for measuring paint surface orange peel and/or distinctness of image comprising: a video monitor opposite the surface to be measured for reflection in the surface, means for generating a succession of grid patterns on the monitor such that images of the patterns on the monitor are reflected by the surface, each grid pattern having a spatial frequency different from the frequencies of the other patterns, electronic means for acquiring the reflected images, and means for analyzing the acquired image to determine a measure of paint surface quality.

BRIEF DESCRIPTION OF THE DRAWINGS

The above and other advantages of the invention will become more apparent from the following description taken in conjunction with the accompanying drawings wherein like references refer to like parts and wherein.

DESCRIPTION OF THE INVENTION

The ensuing description is directed to a paint quality inspection system and method as developed specifically for measuring the quality of automotive finishes. The modulation transfer function is used to determine orange peel as well as distinctness of image.

Both values are useful since each provide information about the painting process and can be used to control the process to correct any tendency to produce unacceptable amounts of each type of surface roughness. The invention is not limited to the automotive application and has other uses where accurate quantification of a paint surface is desired.

The modulation transfer function (MTF) analysis technique is well known for the evaluation of optical systems. A detailed treatment of MTF analysis is given in the text, Warren J. Smith, Modern Optical Engineering (N.Y., McGraw Hill, 1986), which is incorporated herein by reference. In the present application the reflective automative finish is considered to be the optical system. The MTF will provide a measure of how much the reflective images are degraded by this surface, and particularly the degradation due to orange peel and smaller surface roughness features as revealed by distinctness of image measurements. Special measures are taken to avoid any influence of surface curvature in the results.

MTF techniques are a classical method of measuring the optical quality of surface attributes that are smaller than the scale of the MTF bar patterns. The classical MTF techniques, if applied to the measure of distinctness of image and orange peel attributes would require the sensor to be located only a few inches from the optical surface. This would be impractical or undesirable for a moving product line factory environment.

Figure 1:
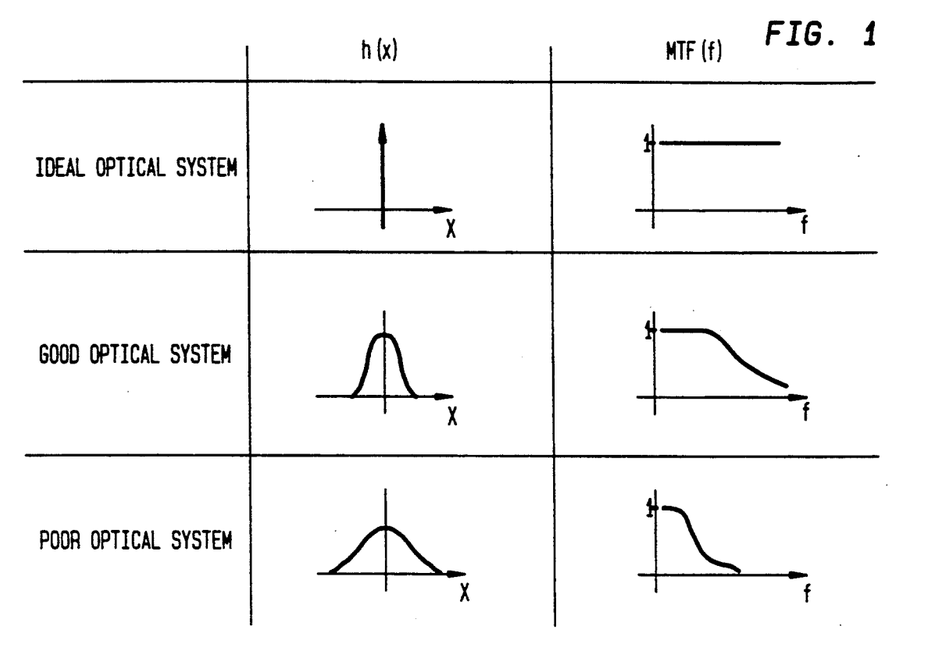
FIG. 1 is a chart showing the optical system impulse response and the corresponding modulation transfer function for different quality systems.

The MTF is a Fourier transform of the optical system impulse h(x) as shown in FIG. 1. For an ideal system (a perfect mirror) the response h(x) translates the optical input to the output without any distortion. The MTF is unity at all spatial frequencies f. A good optical system is something less than perfect and diminishes the output at higher frequencies but the MTF at low spatial frequencies is still unity or nearly so. As the system response h(x) becomes poorer, the MTF is diminished further at low frequencies. Since orange peel comprises large surface features, it affects the transfer at low spatial frequencies and can be measured by analyzing the MTF for low frequencies only. The DOI measurement, however, encompasses both large and small features so that the MTF for both low and high spatial frequencies is used in its determination.

The method of generating the MTF curves is to provide several striped black and white video patterns having different spatial frequencies, cause the patterns to sequentially reflect from the painted surface, detect the reflected image for each pattern by a video camera, and determine the MTF for each spatial frequency. The plot of the MTF's for this measurement sequence is the curve for the particular surface.

The video camera transforms the video image into a series of intensity values (I) that range between 0 for pure black and 255 for the brightest white. For a particular fringe period p (or frequency f=1/p), the maximum and minimum intensities ($I_{max}$, and $I_{min}$,) are found and the contrast C(f) is calculated as follows: $C(f) = 2(I_{max'} - I_{min'})/(I_{max'} + I_{min'})$. By this definition, the highest possible contrast value is e=2. In generating the MTF curve, these contrast measures are obtained for a number of spatial frequencies. The MTF data is the normalization of these contrast values to the maximum measure $C_{max'}$ taken for that surface in the measurement sequence. Thus, $MTF(f) = C(f)/C_{max'}$. Ideally, $C_{max'}$ will occur at the lowest spatial frequency.

Figure 2:
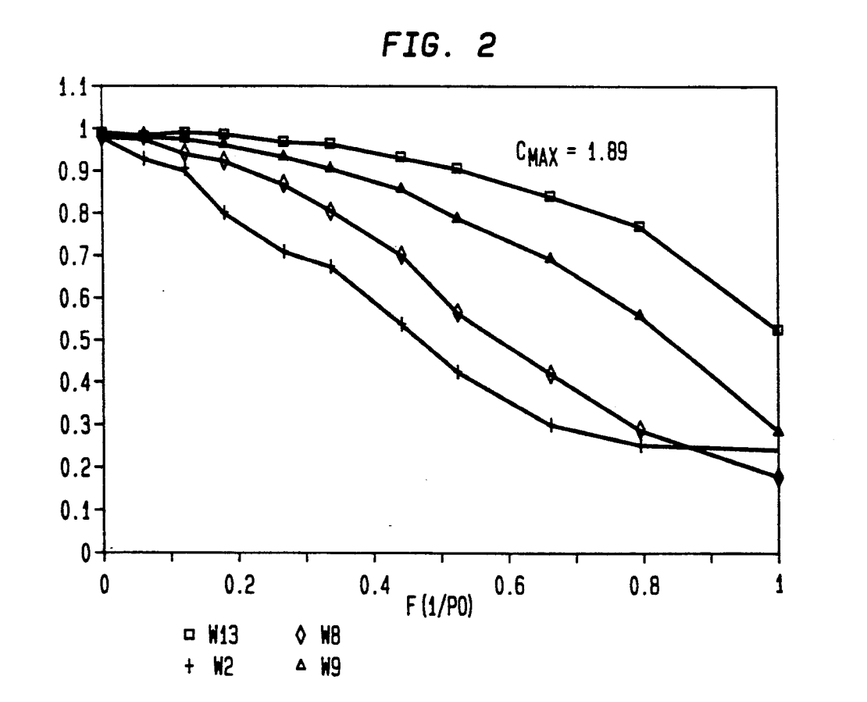
FIG. 2 is a graph illustrating the modulation transfer function measured for four different painted surfaces.

The MTF curves are mathematically correct for a sinusoidal fringe pattern input. In practice it is generally more practical to utilize a solid black-and-white bar input that would ideally appear as a square wave. However, from a practical standpoint for the analysis of these paint surfaces, the high spatial frequencies associated with a square wave are lost in the optical system so that there is essentially no difference in the MTF curves generated by a square pattern or a sinusoidal pattern. An example of MTF curves derived in this manner is given in FIG. 2. The four curves are for four white panels of different surface quality. Eleven different black-and-white bar patterns were presented by a video monitor with the largest spatial frequency f=1 cycle per inch; i.e. the finest video pattern had stripes one half inch wide. In this example, each point on the curves is the average of several MTF measurements at different positions on the same panel. The value of $C_{max'}$ is given for each panel.

Figure 3:
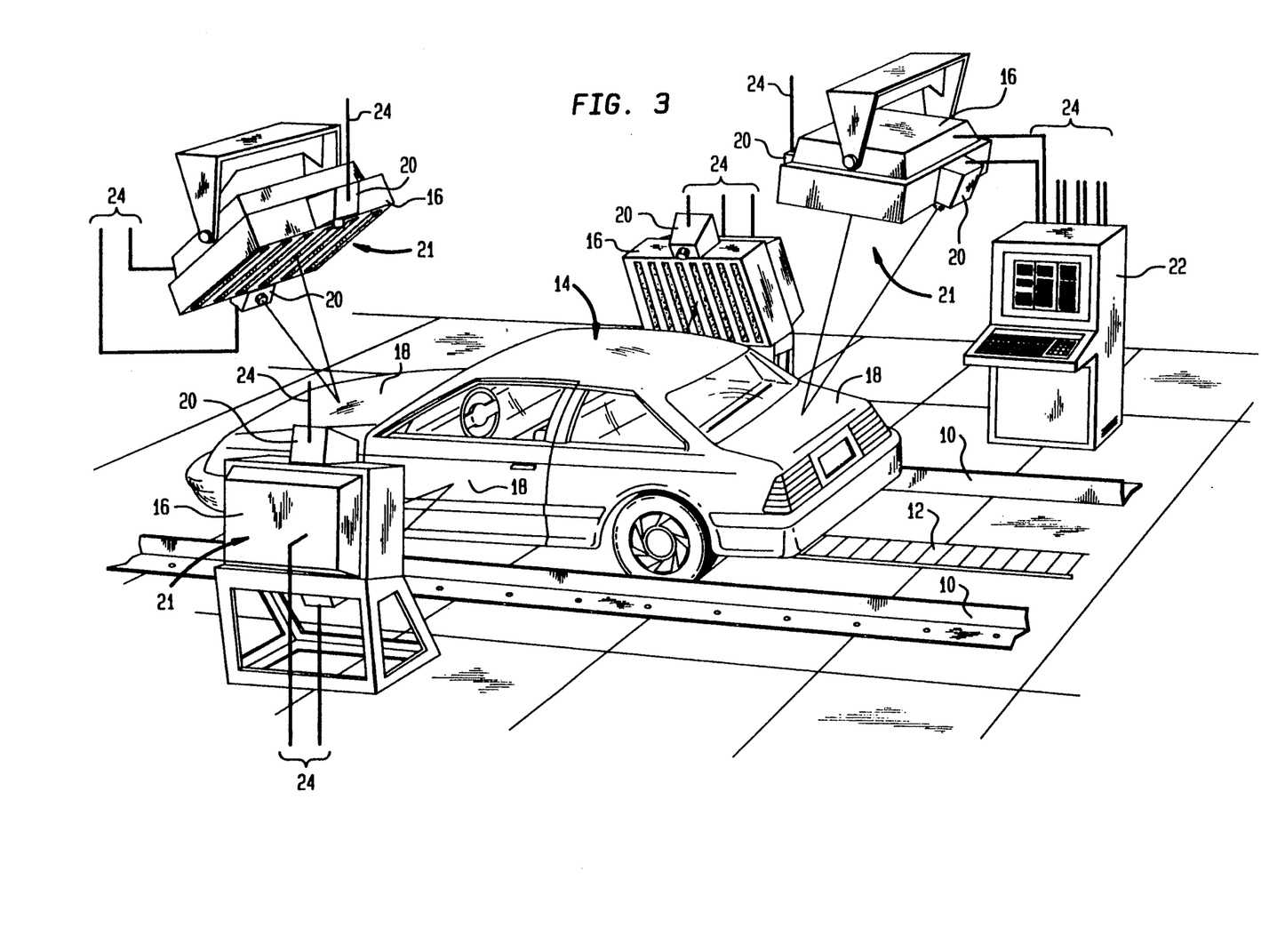
FIG. 3 is a perspective view of a vehicle paint inspection station equipped with apparatus according to the invention.

The MTF measurement system is applied to a painted vehicle as shown is FIG. 3. An inspection station includes guide rails 10 and a conveyor track 12 for moving a vehicle 14 through the station. A number of video monitors 16 are positioned at either side of or above the path of the vehicle at locations spaced from the vehicle as it moves through the station. Each monitor 16 is facing directly toward a panel 18 of the vehicle during at least a portion of the vehicle travel through the station so that the bar pattern on the monitor reflects from the nearest painted surface or panel 18. Two spaced video cameras 20 are positioned adjacent each monitor 16. Each monitor and camera pair is called a sensor 21. Only one of the two cameras 20 is used at a time depending on the angle of light reflectance from the surface. Each camera views the image reflected at a particular angle from the panel 18 and provides a serial output of signals representing a digital profile of the image intensity. The video camera outputs are directed to a computer 22 for analysis of the video signals and determination of the MTF curve for each panel and an objective rating of the orange peel. The computer 22 is also coupled to each monitor 16 for control of the monitors. Lines 24 effect the connection of the computer 22 to the monitors 16 and cameras 20. In its simplest form, assuming the panels are flat, a series of black-and-white bar patterns of standard spatial frequencies are generated by the computer and displayed on the monitors. It has been determined that five patterns having spatial frequencies in the range of about f=2 to f=0.25/in provide sufficient MTF data for the analysis of automotive finishes. The patterns reflected from a panel are viewed by the camera to yield corresponding standard spatial frequencies in the image plane, the video signals are analyzed by the computer and the MTF curve is generated. However, if the panels 18 are not flat, the panel curvature can cause distortion of the image and thus degrade the MTF evaluation. Usually the panels are convex and the image is magnified. The measurement system compensates for curvature by having the computer 22 control the pattern generation on the monitor. For each sequence of patterns an initial reference pattern, which is in addition to the five measurement patterns, is of a known reference spatial frequency. The image viewed by the video camera 20 is analyzed to determine the distortion, if any, in the image and then the five input frequencies required to yield the desired standard spatial frequencies in image space are calculated. This feedback control effects the generation of corrected patterns for display. Each monitor is controlled independently of the others. It is convenient to use the initial reference pattern to determine the value of $C_{max'}$. By continually repeating the measurement process during the vehicle movement a longitudinal series of positions on each panel is evaluated. A functional diagram of this computer control is set forth in FIG. 4.

The matter of correlating the MTF information to subjective orange peel evaluations can be approached in a number of ways since the shape of the MTF curve varies as a function of orange peel or DOI. One method is to choose the MTF value of a particular spatial frequency, say 0.5, and use that as the measure of orange peel. Empirical data reveals that a substantial change in MTF occurs in the region of f=0.5 for a wide variety of surface qualities. Those MTF values are nonlinearly related to the subjective orange peel scale and thus a conversion table or formula may be used to reach an equivalent orange peel rating.

Figure 4:
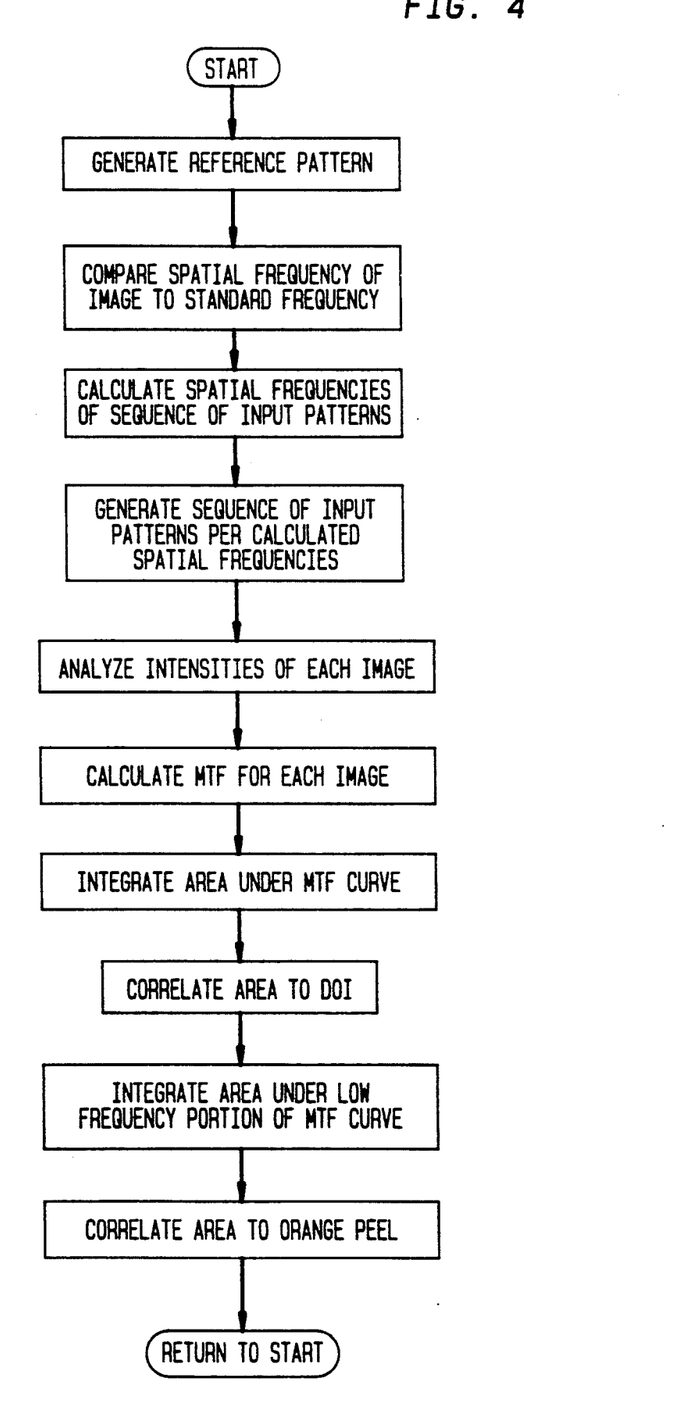
FIG. 4 is a flow diagram illustrating functions performed in carrying out the method of the invention.
Figure 5:
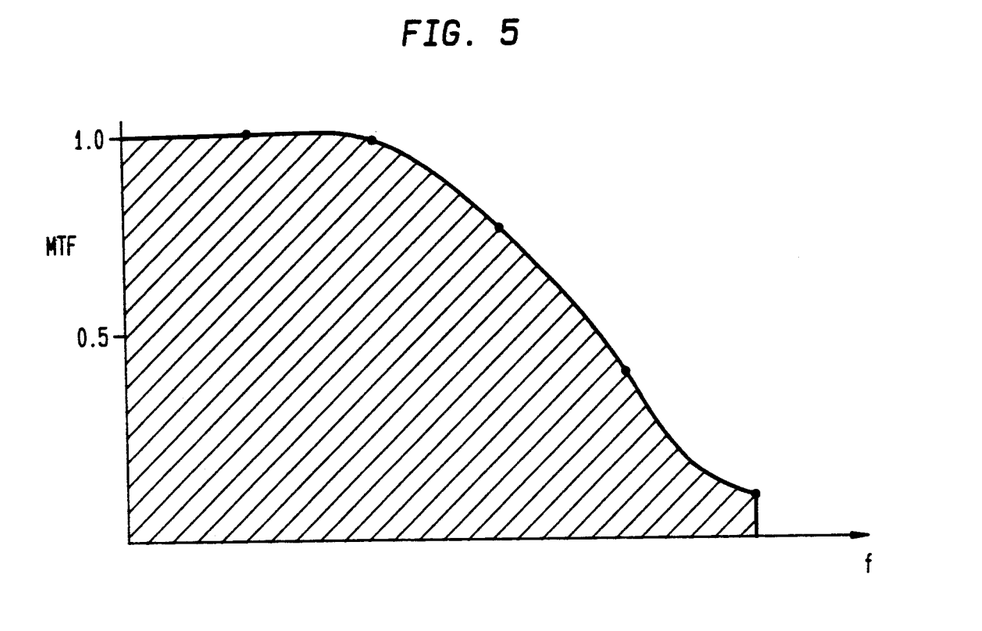
FIGS. 5 and 6 are modulation transfer curves illustrating the measurement of distinctness of image and orange peel respectively, according to the invention.
Figure 6:
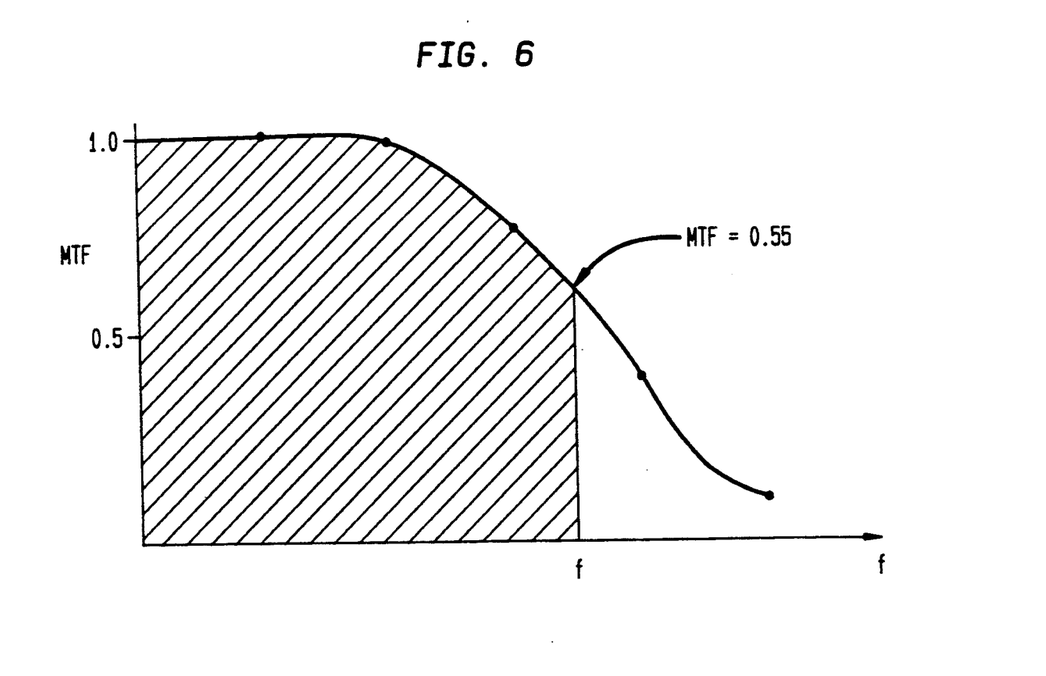

A method included in FIG. 4 which useful to measure DOI is to integrate the area under the MTF curve as shown by the shaded area in FIG. 5. This area is the measure of the strength of the optical impulse response h(x) at all measured frequencies. This is appropriate since the surface artifacts which affect DOI modulate large and small spatial frequencies. This parameter correlates well with subjective evaluations of DOI when the nonlinear conversion is applied. A parameter that is useful in rating orange peel is the area under the MTF curve for frequencies below a certain MTF value. The low spatial frequencies are largely unaffected by surface roughness smaller than orange and thus this region of the MTF information is particularly suitable for such measurement. In practice, the choice of MTF=0.55 has been found to provide the best fit with subjective observations. FIG. 6 illustrates the frequency $f_{op}$ which corresponds to MTF=0.55 and the shaded area under the MTF curve at spatial frequencies less than $f_{op}$. This area is correlated to the subjective orange peel measurements by a conversion table or formula.

Figure 7:
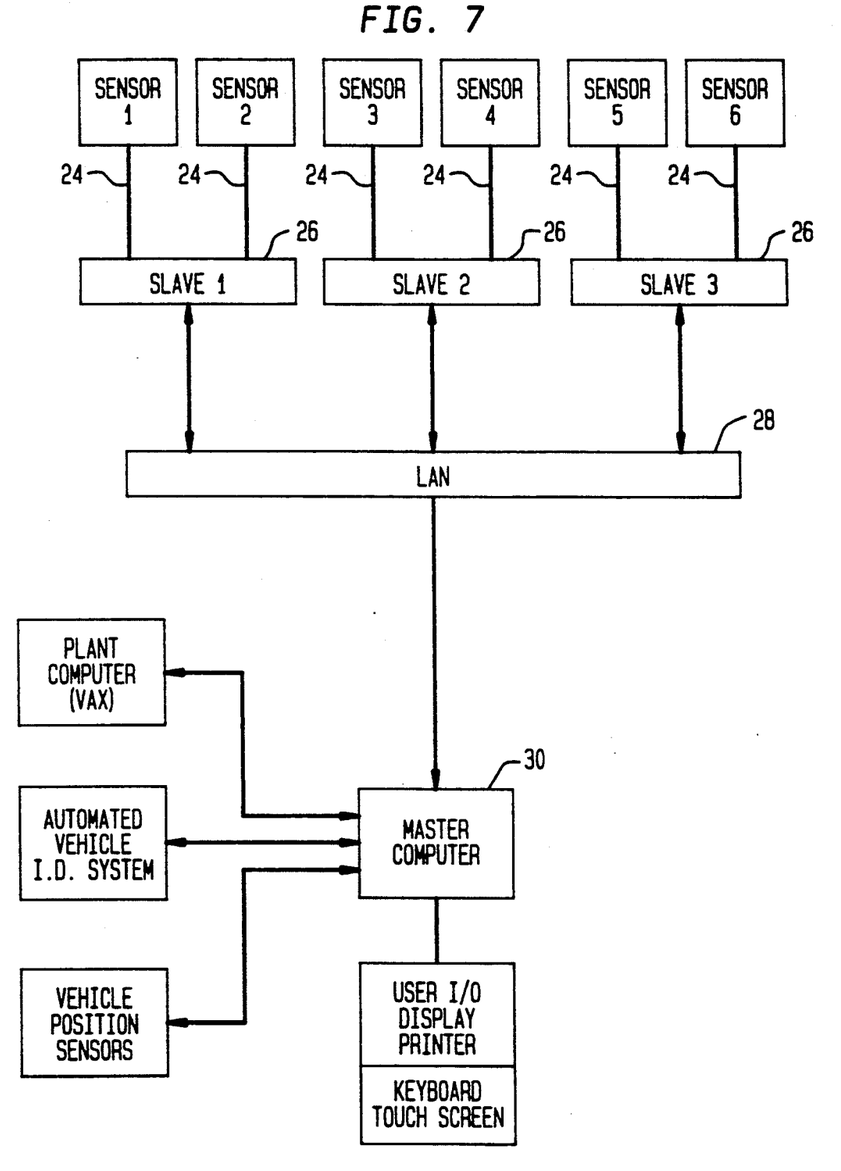
FIGS. 7 and 8 are schematic diagrams of the system used to elevate the paint finish quality according to the invention.

The monitors 16 may be very large to illuminate large areas of the panels and by using more than one video camera per monitor a plurality of regions for each monitor may be evaluated. It is found, however, that smaller monitors in greater numbers allow greater flexibility and ease of mounting. Monitors having 19 inch diagonal measure have been found to be suitable. Preferably the monitors are mounted 50 inches from the painted surface and the cameras are 40 inches from the surface. The cameras are solid state with a high gain setting. The lenses are f/3.5 with a 55 mm focal length. During setup, using a flat reflective surface, it is preferred to focus the cameras on the video monitor although they may instead be focused on the surface. This arrangement permits a field of view of 6×8 inches on the surface. It is advantageous to select a portion of the field of view for analysis; in particular a narrow patch, say ¾ inch by 1½ inches, yields good results. This corresponds with a camera area of 130 columns and 5 rows of cid detectors in the camera. The computer 22 is a microprocessor system as shown in FIG. 7 which employs three slave processors 26 having inputs 24 from the video cameras 20 and outputs fed via a local area network (LAN) 28 to a master computer 30 which i a microprocessor based machine such as an IBM (TM) AT computer. Twelve cameras can be serviced by this arrangement. A user I/O interface includes a display and printer as well as a keyboard and/or a touch screen. The master computer 30 also has inputs and outputs coupled to a plant computer, an automated vehicle identification system and vehicle position sensors. The information sent to the plant computer can be used for adjusting paint processes or for providing quality control data. The vehicle I.D. system provides data on the specific vehicle being monitored and the type of vehicle. The position sensors provide data on the progress of the vehicle through the inspection station which can be used to determine which cameras should be active at any given time and which panels are being inspected.

Figure 8:
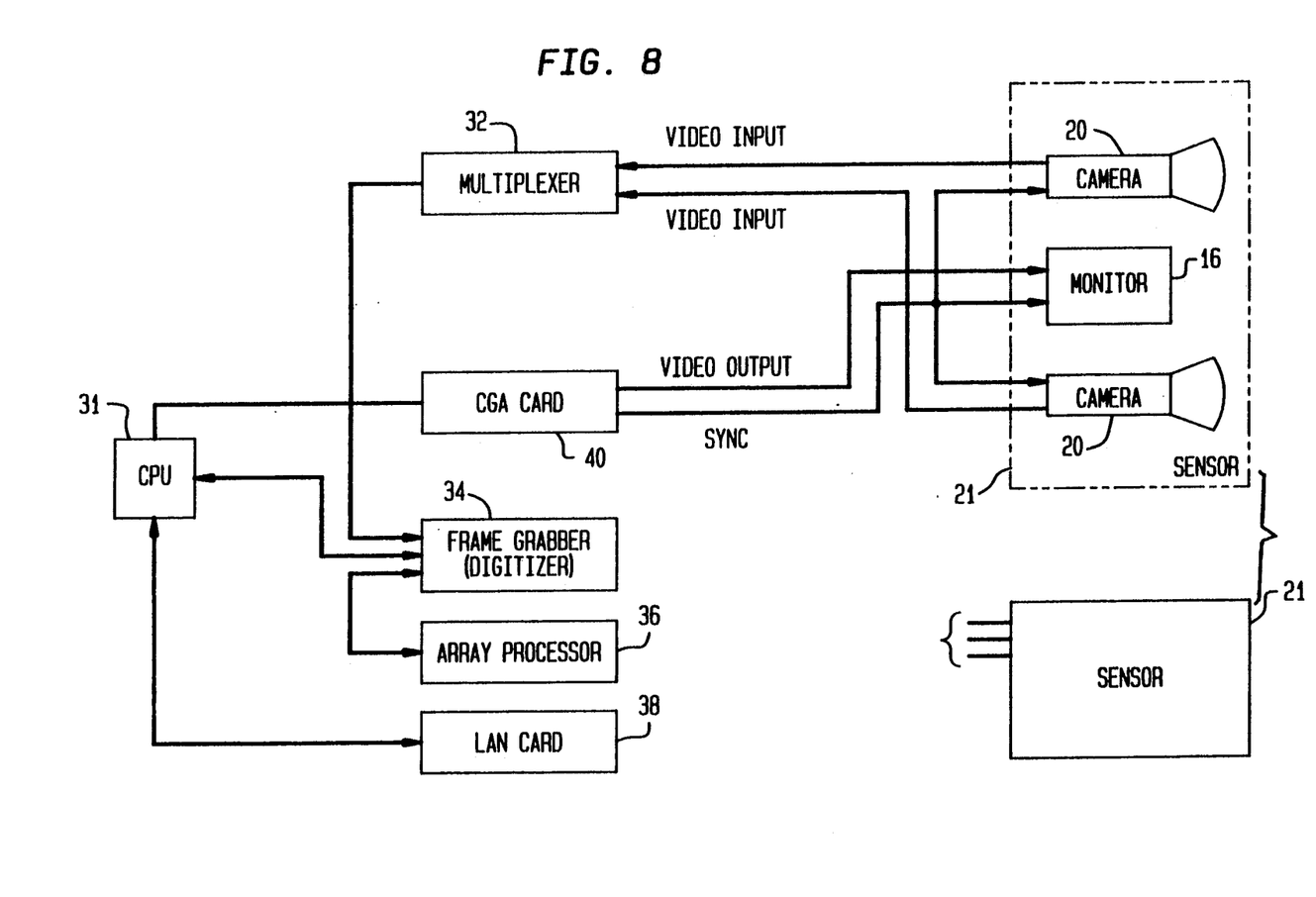

As shown in FIG. 8, each slave unit 26 includes a CPU 31, a multiplexer 32 for receiving analog signals from two sensors 21 (four cameras 20) and selecting one at a time for processing, a frame grabber 34 coupled to the multiplexer and the CPU to digitize and store the camera signals comprising one frame, and an array processor 36 coupled to the frame grabber having parallel processing architecture for selecting a patch to be analyzed and rapidly calculating the MTF for each patch. A LAN card 38 coupled to the CPU 31 affords communication with the master computer. Finally, CGA card 40 connected to the CPU, the cameras 20 and the monitor 16 supplies synch signals to the cameras and the monitor and supplies the video output to the monitor 16. The CGA card generates the grid patterns to control the monitor display. The CPU 31 makes the curvature correction and issues a feedback signal to the CGA card to control the monitor.

With this apparatus, the patterns are generated and displayed at a rate of 0.1 sec each. Thus by using five patterns for each sequence, the sequence is completed in one half second. Due to the use of parallel processing of the camera data the entire calculation of orange peel and DOI is completed in the one half second period. The apparatus is calibrated by placing four previously measured samples or standards in front of each camera/monitor pair. The samples are measured by the system, and the standards numbers are manually entered. A linear regression curve fit is made to the four data points. The resulting coefficients for a given camera are subsequently used for scaling each measure.

This invention has established the fact that the distinctness of image and orange peel effect the MTF curves in a unique manner which permits a long standoff of the camera and fringe monitor. Further, this invention permits a highly desirable and useful system that can be implemented with simple components such as video monitors and video cameras which can be mounted at distances of over two feet from a moving automobile surface.

What is claimed is:

1. The method of measuring the quality of a reflective painted surface comprising the steps of:
    generating a plurality of bar patterns each having a spatial frequency different from the other patterns,
    serially reflecting images of the patterns from the surface to be inspected,
    electronically imaging the reflected patterns,
    analyzing the images and generating modulation transfer function curves,
    establishing modulation transfer functions for surface quality standards, and
    determining the surface quality by correlating the modulation transfer function of the surface with that of the standards.

2. The invention as defined in claim 1 wherein the step of determining the surface quality comprises integrating the area under the modulation transfer function curve, wherein the area correlates to distinctness of image.

3. The invention as defined in claim 1 wherein the step of determining the surface quality comprises integrating the area under the modulation transfer function curve for spatial frequencies less than the point at which the transfer function is approximately the maximum value, wherein the area correlates to orange peel.

4. The invention as defined in claim 1 wherein the step of determining the surface quality comprises integrating the area under the modulation transfer function curve for spatial frequencies less than the point at which the transfer function is 0.55 times the maximum value, wherein the area correlates to orange peel.

5. The invention as defined in claim 1 wherein the step of generating a plurality of bar patterns comprises generating a first pattern, measuring the spatial frequency in the reflected image of the first pattern, and controlling the subsequent patterns to yield reflected images having desired spatial frequencies.

6. The invention as defined in claim 1 as applied to a curved painted surface which distorts the reflected image wherein the step of generating a plurality of bar patterns comprises generating a first pattern having a known spatial frequency, evaluating the image of the first pattern to determine the amount of curvature distortion, and then compensating for the curvature distortion by calculating the spatial frequencies of the subsequent pattern required of yield images having the required spatial frequencies and controlling the subsequent patterns to the calculated spatial frequencies.

7. The invention as defined in claim 1 wherein the steps are accomplished in less than one second.

8. The invention as defined in claim 1 including the step of continuously moving the painted surface in a path to obtain successive surface quality determinations along the path of movement.

9. A system for measuring the quality of a reflective painted surface comprising:
 a video monitor opposite the surface to be measured for reflection in the surface,
 means for generating a succession of grid patterns on the monitor such that images of the patterns on the monitor are reflected by the surface, each grid pattern having a spatial frequency different from the frequencies of the other patterns,
 electronic means for acquiring the reflected images, and
 means for analyzing the acquired images and for correlating with surface quality standards to determine a measure of paint surface quality.

10. A system for measuring the quality of a reflective painted surface comprising:
 a video monitor positioned opposite the surface to be measured for reflection in the surface,
 microprocessor means for generating a succession of grid patterns of different spatial frequencies on the monitor such that images of the patterns on the monitor are reflected by the surface,
 a video camera opposite the surface for viewing the image reflected from the surface,
 the microprocessor means including means for analyzing the acquired images, for calculating the modulation transfer function of the paint surface from the various images and for correlating with the modulation transfer function of surface quality standards to determine a measure of paint surface quality.

11. The invention as defined in claim 10 wherein the means for calculating the modulation transfer function also determines the area under the modulation transfer function curve and correlates the area to the quality of the painted surface.

12. A system for measuring paint surface quality on an automotive vehicle having reflective paint comprising:
 a test station including means for moving vehicles through the station,
 a plurality of video monitors positioned opposite the vehicle surface and spaced from the surface,
 microprocessor means for generating a succession of grid patterns of different spatial frequencies on each monitor such that images of the patterns on the monitors are reflected by various regions on the surface,
 video camera means opposite the vehicle and spaced from the surface for viewing the images reflected from the surface,
 the microprocessor means including means for analyzing the acquired images, for calculating the modulation transfer function of the paint surface from the various images and for correlating with the modulation transfer function of surface quality standards to determine a measure of paint surface quality at each region.

* * * * *